US00RE38426E

(19) United States
(12) Reissued Patent
Bonnet et al.

(10) Patent Number: US RE38,426 E
(45) Date of Reissued Patent: Feb. 10, 2004

(54) 5-O-DEOSAMINYL 6-O-METHYL ERYTHRONOLIDE A DERIVATIVES, PREPARATION METHOD THEREFOR AND USE THEREOF FOR PREPARING BIOLOGICALLY ACTIVE MATERIALS

(75) Inventors: Alain Bonnet, Chateau Thierry (FR); Bernadette Chappert, Paris (FR); Jacques Lagouardat, Noisy le Grand (FR)

(73) Assignee: Aventis Pharma S.A. (FR)

(21) Appl. No.: 09/772,277

(22) PCT Filed: Oct. 8, 1996

(86) PCT No.: PCT/FR96/01567

§ 371 (c)(1),
(2), (4) Date: Apr. 20, 1998

(87) PCT Pub. No.: WO97/13774

PCT Pub. Date: Apr. 17, 1997

Related U.S. Patent Documents

Reissue of:
(64) Patent No.: 6,011,142
Issued: Jan. 4, 2000
Appl. No.: 09/051,378
Filed: Apr. 20, 1998

(30) Foreign Application Priority Data

Oct. 9, 1995 (FR) ..... 95 11861

(51) Int. Cl.[7] ..... C07H 17/00; A61K 31/70
(52) U.S. Cl. ..... 536/7.4; 536/7.2; 514/29
(58) Field of Search ..... 536/7.2, 7.4; 514/29

(56) References Cited

U.S. PATENT DOCUMENTS 3,923,784 A * 12/1975 Kierstead et al. ..... 536/7.2
4,518,590 A * 5/1985 Hauske et al. ..... 514/29
4,742,049 A * 5/1988 Baker et al. ..... 514/29
4,921,839 A * 5/1990 Brain et al. ..... 514/29
5,631,355 A * 5/1997 Asaka et al. ..... 536/7.4

FOREIGN PATENT DOCUMENTS

EP 0619320 10/1994
EP 0638585 2/1995
EP 0682038 11/1995

OTHER PUBLICATIONS

Journal of Medicinal Chemistry, vol. 18, No. 8, pp. 849–851, 1975.*

* cited by examiner

*Primary Examiner*—James O. Wilson
*Assistant Examiner*—Howard V. Owens, Jr.
(74) *Attorney, Agent, or Firm*—Muserlian, Lucas and Mercanti

(57) ABSTRACT

A subject of the invention is the compounds of formula (I):

[ (I)

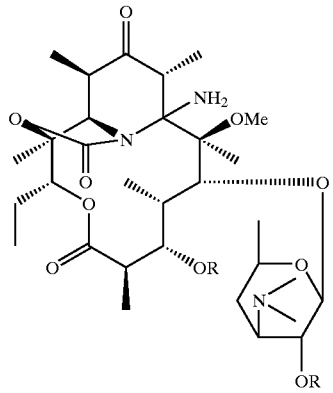

] (I)

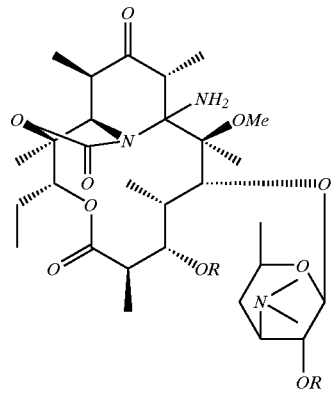

in which R represents a carboxylic acid remainder containing up to 18 carbon atoms the products of formula (I) can be used to prepare antibiotic products.

7 Claims, No Drawings

5-O-DEOSAMINYL 6-O-METHYL ERYTHRONOLIDE A DERIVATIVES, PREPARATION METHOD THEREFOR AND USE THEREOF FOR PREPARING BIOLOGICALLY ACTIVE MATERIALS

Matter enclosed in heavy brackets [ ] appears in the original patent but forms no part of this reissue specification; matter printed in italics indicates the additions made by reissue.

This application is a 371 of PCT/FR96/01567 filed on Oct. 8, 1996.

The present invention relates to new derivatives of 5-O-desosaminyl 6-O-methyl erythronolide A, their preparation process and their use in the preparation of biologically active products.

A subject of the invention is the compounds of formula (I):

[

(I)

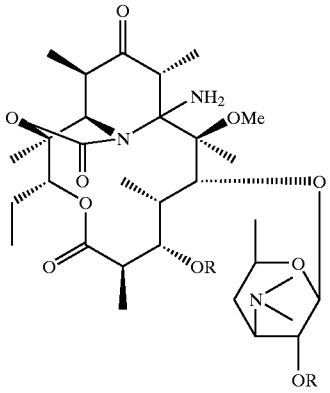

]

*(I)*

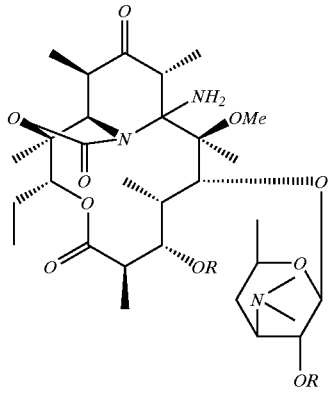

in which R represents a carboxylic acid remainder containing up to 18 carbon atoms.

Among the carboxylic acid remainders, there can in particular be mentioned the acetyl, propionyl, butyryl, isobutyryl, n-valeryl, isovaleryl, tert-valeryl and pivalyl radicals.

A more particular subject of the invention is the compounds of formula (I) in which R represents an acetyl radical.

A subject of the invention is also a preparation process characterized in that a compound of formula (II):

[

(II)

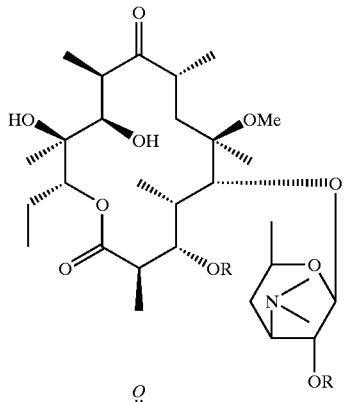

*(II)*]

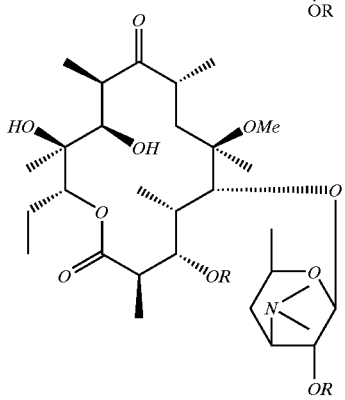

in which R retains its previous meaning, is subjected to the action of an agent capable of selectively activating the hydroxyl in position 11, then to the action of a base to obtain the compound of formula (III):

[

(III)

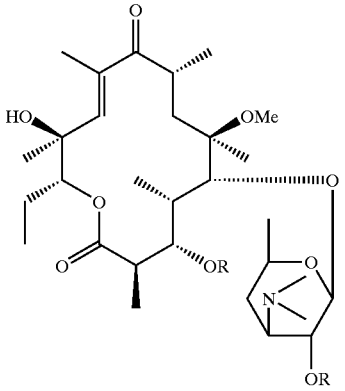

]

*(III)*

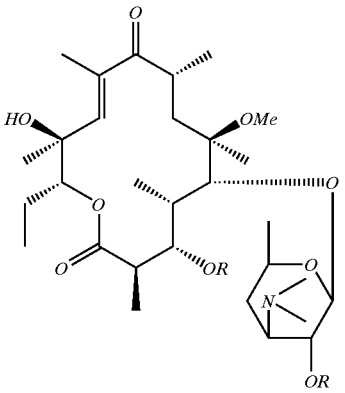

which is subjected to the action of carbonyldiimidazole, then to the action of the hydrazine $NH_2NH_2$ to obtain the corresponding compound of formula (I).

The compounds of formula (II) we known in a general way and can be prepared according to the process described in European Patent Application 619319.

In a preferred implementation, the agent capable of selectively activating the hydroxyl in position 11 is a sulphonic add derivative such as methanesulphonic, paratoluenesulphonic, trifluoromethanesulphonic anhydride or thionyl chloride $SOCl_2$, which forms a cyclic sulphite with the OH function in position 12, the base used to produce a 10(11) double bond is a diazabicycloundecene, for example DBU (or 1,8-diazabicyclo-[5-4-0]undec-7-ene), or DBN (or 1,5-diazabicydo[4,3,0]non-5-ene or 2,6-lutidine, a 2,4,6-collidine or tetramethyl-guanidine, the reaction of the compound of formula (III) with carbonyldiimidazole takes place in the presence of one of the bases mentioned above or also in the presence of sodium hydride, triethylamine, sodium or potassium carbonate or bicarbonate. $NaN(SiMe_2)_2$ a $LiN(SiMe_3)_2$, the hydrazine is used in the form of hydrazine hydrate.

The obtained compounds of formula (III) are new products and are themselves a subject of the present invention.

The subject of the invention is therefore, as chemical products, the compounds of formula (III) and quite particularly the compound of formula (III) in which R represents an acetyl radical.

The compounds of formula (I) are useful intermediate products which can in particular lead to the preparation of antibiotic products, described and claimed in European Patent Application 0,676,409.

In particular, a subject of the invention is the use, characterised in that a compound of formula (I) is subjected to the action of a cleaving agent of the protected hydroxyl functions to obtain the compound of formula (IV):

[

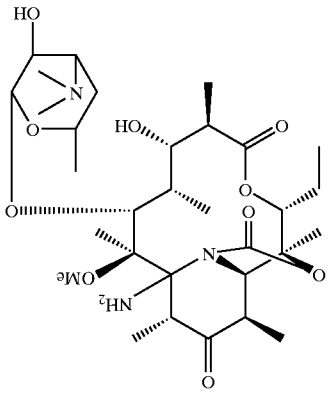

]

-continued (IV)

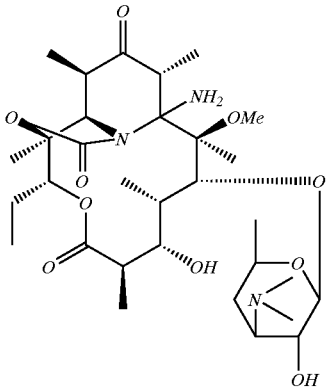

which is subjected to the action of an aldehyde of formula (V):

(V)

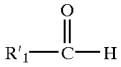

in which $R'_1$ represents a hydrogen atom or a saturated or unsaturated hydrocarbon radical containing up to 23 carbon atoms, optionally interrupted by one or more heteroatoms and optionally having one or more functional groups, to obtain the compound of formula (VI):

[

(VI)

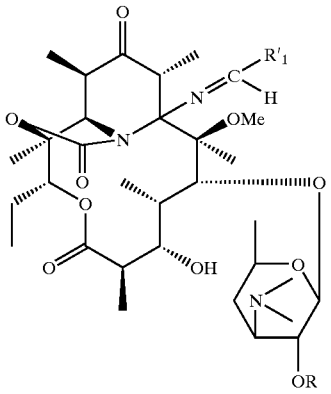

]

(VI)

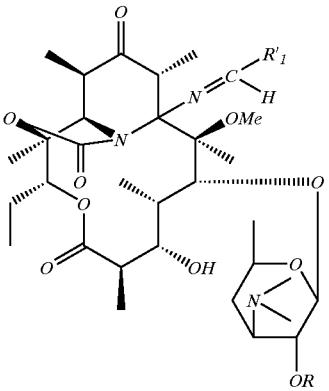

which is subjected to the action of an oxidizing agent of the hydroxyl in position 3 then to the action of a cleaving agent of the hydroxyl in position 2' to obtain the compound of formula (VII):

[ (VII)

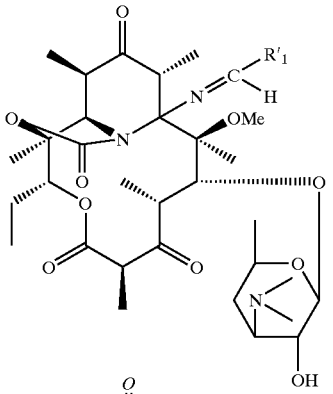

(VII)]

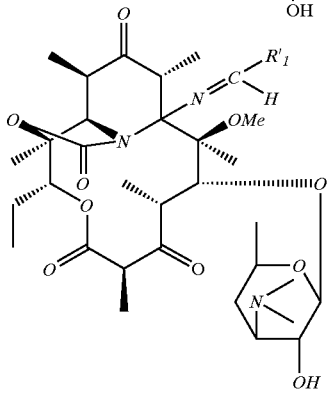

which is subjected to the action of a reducing agent to obtain the corresponding compound of formula (VIII):

[ (VIII)

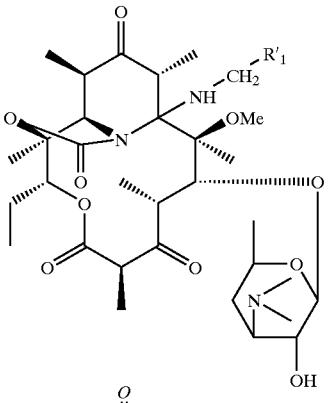

(VIII)]

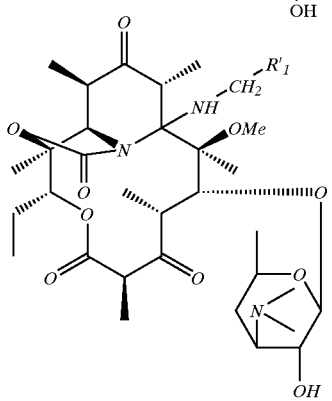

in which $R'_1$ retains its previous meaning.

In a preferred implementation, $R'_1$ represents the radical

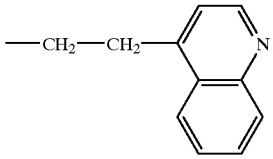

cleavage of the protected hydroxyl functions is carried out by saponification then acidification of the ester function, esterification of the hydroxyl function in position 2' is carried out according to standard processes, oxidation of the hydroxyl in position 3 is carried out using a diimide in the presence of DMSO, for example the hydrochloride of 1-ethyl 3-(3-dimethylamino propyl) carbodiimide, cleavage of the hydroxyl in position 2' takes place by methanolysis, the reducing agent is $NaBH_3CN$ or $NaBH(OAc)_3$ or also $NaBH_4$ in the presence of acetic acid or hydrogen in the presence of a catalyst such as palladium, platinum and optionally in the presence of an acid such as hydrochloric acid or acetic acid.

The products of formula (VII) are products having useful antibiotic properties, described and claimed in European Patent 0,676,409.

EXAMPLE 1

2',3-diacetate of 11,12-dideoxy-3-de(2.6-dideoxy-3-C-methyl-3-O-methyl-alpha-L-ribohexopyranosyl)-11,12-(hydrazono(carbonyloxy)-6-O-methyl erythromycin

STAGE A

2',3-diacetate of 11-deoxy-10,11-didehydro-3-de(2,6-dideoxy-3-C-methyl-3-O-methyl-alpha-L-ribohexopyranosyl)-6-O-methyl-erythromycin A solution containing 9.45 g of 2',3-diacetate of 3-de-(2,6-dideoxy-3-C-methyl-3-O-methyl-alpha-L-ribohexopyranosyl)-6-O-methyl-erythromycin and 112 ml of pyridine is maintained under agitation at 0° C. for 15 minutes. 1.52 ml of thionyl chloride is added over 10 minutes. Agitation is continued overnight at ambient temperature. Separation and drying are carried out. The resultant product is poured into a mixture of 150 ml of ethyl acetate and 200 ml of sodium bicarbonate. Agitation is carried out for 10 minutes. Decantation is carried out, then extraction with ethyl acetate and drying. 10.7 g of product is obtained A mixture of 10.7 g of this product and 124 ml of dimethyl-formamide is agitated at 50° C. 2.53 ml of DBU is added over 5 minutes. Agitation is carried out for 48 hours at 50° C., and the mixture is then poured into water. 100 $cm^3$ of ethyl acetate is added. Decantation is carried out, and the resultant product is washed with water (1.25 l), extracted with ethyl acetate (400 ml) and dried over magnesium sulphate, then filtered and the filtrate is evaporated to dryness. Approximately 50 ml of isopropyl ether is added and the imixture is left to crystallize for 72 hours, filtered, rinsed and dried. 5.514 g of desired product, which melts at 174° C., is obtained.

STAGE B

2',3-diacetate of 11,12-dideoxy-3-de(2,6-dideoxy-3-C-methyl-3-O-methyl-alpha-L-ribohexopyranosyl)-11,12-(hydrazono(carbonyloxy)-6-O-methyl erythromycin A mixture containing 2.623 g of product prepared in the preceding stage, 972 mg of carbonyldiimidazole, 30 ml of dichloromethane and 60 pl of DBU is agitated. Agitation is maintained for 4 hours. 404 μl of hydrazine hydrate is added. Agitation is carried out for 24 hours, and 50 ml of 0.5 M sodium acid phosphate is added. The mixture is decanted and the resultant product is extracted with methylene chloride and dried. The product is taken up in isopropyl ether. The mixture is left to crystallize overnight. Filtration, rinsing with isopropyl ether and drying are carried out. 2.415 g of desired product is obtained.

| NMR CDCl, ppm | |
|---|---|
| 0.84 (t) | $CH_3$—$CH_2$ |
| 1.00 (d) 1.10 (d) | |
| 1.12 (d)–1.15 (d) | CH—Me's |
| 1.23 (d) | |
| 1.28 (s) | 6 and 12 Me |
| 1.40 (s) | |
| 2.09 (s) | OAc's |
| 2.18 (s) | |
| 2.26 (s) | $NMe_2$ |
| 2.61 (m) (2H) | $H_2$ and $H_3$ |
| 2.88 (m) | $H_2$ |
| 3.00 (m) | $H_{10}$ |
| 3.02 (s) | C—OMe |
| 3.33 (m) | $H_5$ |
| 3.67 (s) | $H_{12}$ |
| 3.69 (d) | $H_5$ |
| 4.03 (d) | $H_1$ax |
| 4.53 (bs) (2H) | $NH_2$ |
| 4.73 (dd) | $H_2$ax |
| 5.03 (d) | $H_3$ |
| 5.13 (dd) | $H_{13}$ |

USE 11,12-dideoxy-3-de((2,6-dideoxy-3-C-methyl-3-O-methyl-alpha-L-ribohexopyranosyl)oxy) 6-O -methyl 3-oxo 12,11-(oxycarbonyl)(2-(3-(4-quinolinyl)2-propyl) hydrazono)) erythromycin

STAGE A 11, 1 2-dideoxy-3-de(2,6-dideoxy-3-C-methyl-3-O-methyl-alpha-L-ribohexopyranosyl) 11,12-(hydrazono (carbonyloxy) 6-O-methyl erythromycin A mixture containing 714 mg of product from Example 1 Stage B, 7.5 ml of isopropanol and 2 ml of N soda is agitated for 30 minutes. The reaction mixture is maintained at ambient temperature for 48 hours. 2 ml of a normal hydrochloric and solution is added. The mixture is evaporated to dryness. The product obtained is chromatographed on silica, eluting with an ethyl acetate-triethylamine (9-1) mixture. 300 mg of desired product is obtained.

STAGE B

2'-acetate of 11,12-dideoxy-3-de(2,6-dideoxy-3-C-methyl-3-O-methyl-alpha-L-ribohexopyranosyl) 12,11-(oxycarbonyl) (3-(4-quinolinyl) propylidene) hydrazono) 6-O-methyl erythromycin 281 ml of 4-quinolinylpropanaldehyde, 10.2 ml of toluene, 802 mg of product prepared in the preceding stage and 306 μl of acetic acid are maintained under agitation and a nitrogen atmosphere for 4 hours. The mixture is evaporated to dryness. The product obtained is chromatographed on silica, eluting with an ethyl acetate-triethylamine (95-5) mixture, then with an ethyl acetate-triethylamine (90-10) mixture. 916 mg of the product is obtained.

839 mg of this product, 10 ml of methylene chloride and 121 μl of acetic anhydride are maintained under agitation overnight. 8.55 ml of ammonia water is added. Agitation is carried out for 10 minutes, the product is extracted with methylene chloride and dried. 846 mg of desired product is obtained

STAGE C 11,12-dideoxy-3-de((2.6-dideoxy-3-C-methyl-3-O-methyl-alpha-L-ribohexopyranosyloxy)3-oxo 12,11-(oxycarbonyl (3-(4-quinolinyl) propylidene) hydrazono)) 6-O-methyl erythromycin A mixture containing 1.783 g of 1-ethyl 3-(3-dimethylamino propylcarbodiimide) hydrochloride. 1.67 ml of DMSO and 11 ml of methylene chloride is agitated for 15 minutes. 781 mg of product prepared in the preceding stage and 8 ml of methylene chloride are added. The mixture is maintained under agitation for 1.30 hours and 1.8 g de pyridinium trifluoroacetate is added. Agitation is carried out for 3 hours at ambient temperature, and 30 ml of ammonium hydroxide is added. Agitation is maintained for 15 minutes, extraction with methylene chloride and drying over magnesium sulphate are carried out. The product is chromatographed on silica, eluting with an ethyl acetate-triethylamine (9-1) mixture 647 mg of product is collected. A mixture of 566 mg of this product and 18 ml of methanol is maintained under agitation overnight and 540 mg of desired product is obtained.

STAGE D 11,12-dideoxy 3-de((2,6-dideoxy 3-C-methyl 3-O-methyl alpha-L-ribohexopyranosyl) oxy) 6-O-methyl 3-oxo 12,11 (oxycarbonyl (2-(3-(4-quinolinyl) 2-propyl) hydrazono)) erythromycin 0.38 g of product prepared in the preceding stage and 38 mg of platinum oxide are dissolved in 10 ml of ethyl acetate. Hydrogenation is carried out for 24 hours under vigourous agitation. The mixture is filtered, rinsed with ethyl acetate and evaporated under reduced pressure. 0.375 g of product is obtained, which is taken up in 5 ml of methanol, 175 μl of acetic acid and 90 mg of sodium borohydride. Agitation is carried out for 3 hours at ambient temperature. The methanol is driven off and the product is taken up in a methylene chloride-water mixture. The pH is adjusted to 8-9 with a 28% ammonium hydroxide solution. Decantation is carried out, the product is washed with water, dried filtered and evaporated to dryness. 0.37 g of product is obtained which is chromatographed on silica, eluting with an ethyl acetate-triethylamine 96-4 mixture. 127 mg of a product (rf=0.25) is obtained which is separated off, washed and dried 90 mg of the desired product M.p.=189° C. is obtained.

NMR $CDCl_3$ ppm, 300 MHz 1.34 (s)–1.48 (s): 6 and 12 $CH_3$; 2.30 (s): $N(CH_3)_2$; 2.65 (s): 6-$OCH_3$; 3.06 (dq): $H_4$; 3.19 (q): $H_{10}$; 3.74 (s): $H_{11}$; 5.50 (mobile t.): NH—$CH_2$; 7.30 (d): $H_3$ quinoline; 7.53–7.68 (dt): $H_6$–$H_7$ quinoline; 8.10 (m): $H_5$–$H_8$ quinoline; 8.79 (d): $H_2$ quinoline.

We claim:

1. A compound of the formula

[ I

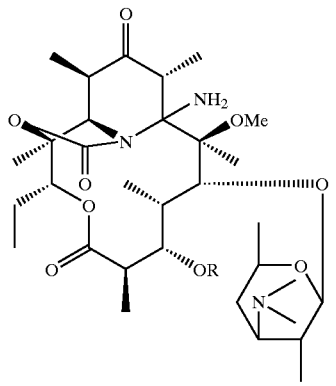

]

-continued (I)

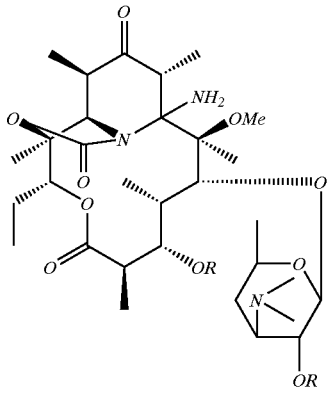

in which R is an aryl of a carboxylic acid of 1 to 18 carbon atoms.

2. A compound of claim 1, in which R is acetyl.

3. A process for the preparation of a compound of claim 1, comprising selectively activating the 11-hydroxyl of a compound of the formula

II

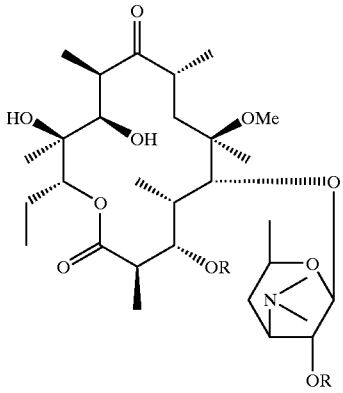

in which R is defined as in claim 1 with an agent capable of selectively activating the hydroxyl in position 11, reacting the resulting product with a base to obtain the compound of the formula

III

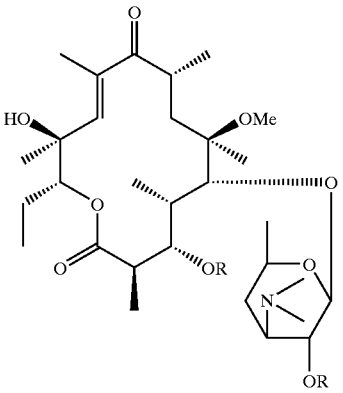

reacting the latter carbonyldiimidazole, then with hydrazine $NH_2NH_2$ to obtain the corresponding compound of formula (I).

4. A process for the preparation of the compound of formula

[ VIII

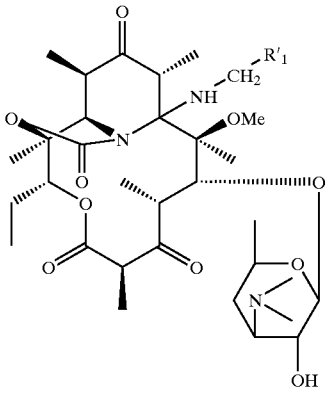

] VIII

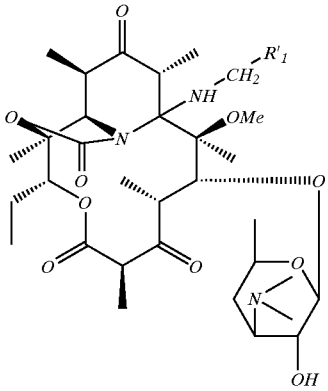

wherein $R'_1$ is selected from the group consisting of hydrogen and an saturated or unsaturated hydrocarbon of up to 23 carbon atoms uninterrupted or interrupted by at least one heteroatom comprising reacting a compound of the formula (I)

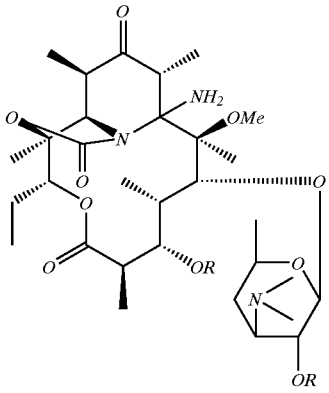

[ IV

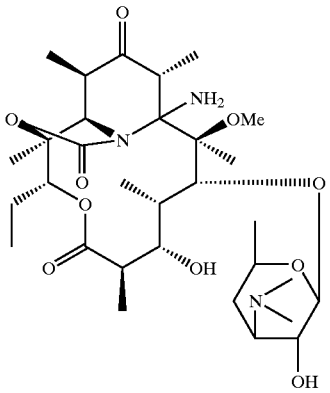

]

with a cleaving agent for the protected hydroxy functions, then subjecting the resulting product [to the reaction with an aldehyde] of the formula

V

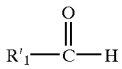

to the reaction with an aldehyde of the formula (IV)

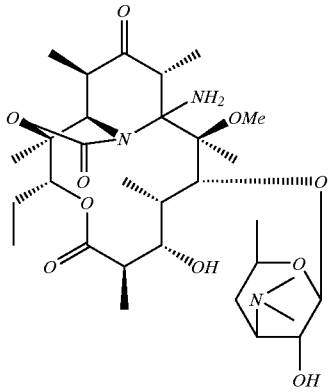

wherein $R'_1$ has the above definition to obtain a compound of the formula

[ VI

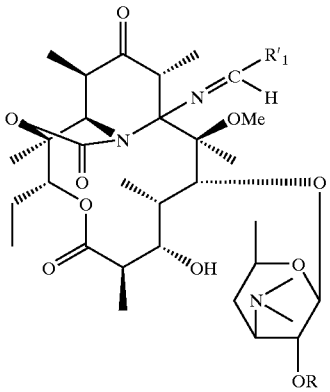

]

-continued (VI)

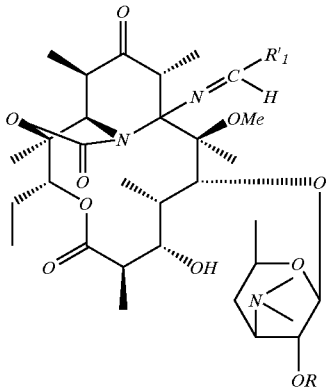

and subjecting the latter to an oxidizing agent for the 3 hydroxyl group and then to the action of a cleaving agent for the 2'-hydroxyl group to obtain the compound of Formula *VII and subjecting the latter to the action of a reducing agent to obtain a compound of formula* VIII.

5. The process of claim 4 wherein $R'_1$ has the formula

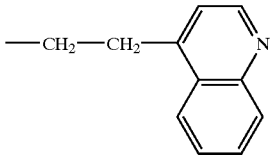

6. A compound of the formula

[ III

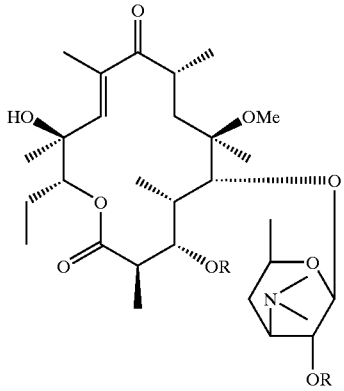

(III)]

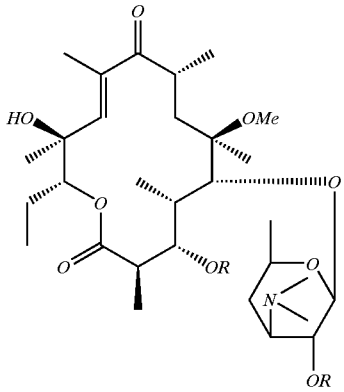

wherein R is an acyl of an organic carboxylic acid of 1 to 18 carbon atoms.

7. A compound of claim 6 wherein R is acetyl.

* * * * *